United States Patent [19]

Biollaz

[11] 4,424,159

[45] Jan. 3, 1984

[54] PROCESS FOR THE SYNTHESIS OF THE HYDROXYACETYL SIDE-CHAIN OF STEROIDS OF THE PREGNANE TYPE, NOVEL 21-HYDROXY-20-OXO-17α-PREGNANE COMPOUNDS AND PHARMACEUTICAL PREPARATIONS CONTAINING THEM

[75] Inventor: Michel Biollaz, Riehen, Switzerland

[73] Assignee: Ciba-Geigy Corporation, Ardsley, N.Y.

[21] Appl. No.: 345,309

[22] Filed: Feb. 3, 1982

Related U.S. Application Data

[63] Continuation of Ser. No. 165,906, Jul. 3, 1980, abandoned, which is a continuation of Ser. No. 37,555, May 9, 1979, abandoned.

[30] Foreign Application Priority Data

May 26, 1978 [CH] Switzerland ............ 5778/78

[51] Int. Cl.³ .................. C07J 33/00; C07J 5/00
[52] U.S. Cl. ................ 260/239.5; 260/397.1; 260/397.4; 260/397.45; 260/397.47; 424/241
[58] Field of Search .......... 424/241; 260/397.47, 260/397.45, 397.4, 239.5

[56] References Cited

U.S. PATENT DOCUMENTS 3,039,926  6/1962  Shull .................. 260/397.45
3,250,792  5/1966  Wettstein et al. ............ 260/397.1
4,155,923  5/1979  Neef et al. ............... 260/397.1

FOREIGN PATENT DOCUMENTS 2442616  3/1976  Fed. Rep. of Germany ... 260/397.1

OTHER PUBLICATIONS

Fieser & Fieser, "Steroids", pp. 566–567.
Helv. Chim. Acta 23 (1940), C. W. Shoppe, p. 927.
Journ. Amer. Chem. Soc. (1954), vol. 76, pp. 2026–2027.
Chemical Abstracts, vol. 85, 1976, p. 568.
Ogura et al., Tetrahedron Letters, 2681–2684 (1972).

*Primary Examiner*—Elbert L. Roberts
*Attorney, Agent, or Firm*—Irving N. Feit

[57] ABSTRACT

The present invention relates to a novel general process for synthesizing a α- or β-oriented hydroxyacetyl side chain of steroids of the pregnane type, which comprises treating a corresponding steroid carbaldehyde in succession with formaldehyde dimethylmercaptal-S-oxide in the form of an alkali metal salt thereof, and with a strongly acid hydrolysing agent.

Preferred final products are compounds of the formula

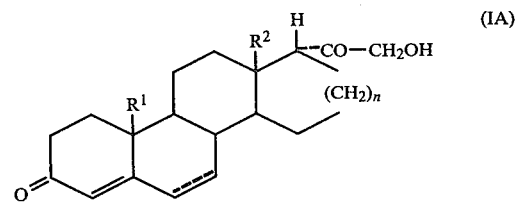

wherein n is 1 or 2, $R^2$ represents methyl or difluoromethyl, and $R^1$ represents hydroxymethyl, methoxymethyl, acetoxymethyl or hydrogen, and, if n is 2 and/or $R^2$ is difluoromethyl, $R^1$ also represents methyl. These compounds act as agonists or antagonists of natural steroid hormones. The antigestagenic 19,21-dihydroxy-17α-pregn-4-ene-3,20-dione and its 6,7-dehydro derivatives and diacetates are of particular interest.

14 Claims, No Drawings

PROCESS FOR THE SYNTHESIS OF THE HYDROXYACETYL SIDE-CHAIN OF STEROIDS OF THE PREGNANE TYPE, NOVEL 21-HYDROXY-20-OXO-17α-PREGNANE COMPOUNDS AND PHARMACEUTICAL PREPARATIONS CONTAINING THEM

This is a continuation of application Ser. No. 165,906 filed on July 3, 1980, now abandoned which in turn is a continuation of application Ser. No. 037,555, filed on May 9, 1979, now abandoned.

The present invention relates in particular to a novel general process for synthesising a α- or β-oriented hydroxyacetyl side chain of steroids of the pregnane type, which comprises treating a corresponding steroid carbaldehyde in succession with formaldehyde dimethylmercaptal-S-oxide in the form of an alkali metal salt thereof, and with a strongly acid hydrolysing agent.

A large number of 21-hydroxy-20-oxo-17β-pregnane compounds are known as therapeutically valuable substances with the action of natural corticoids, i.e. of adrenocortical hormones, or they can be used as intermediates for obtaining such active substances. Hitherto, these compounds have principally been obtained by introducing an unsubstituted or acylated hydroxyl group into the 21-position of a corresponding 21-unsubstituted 20-oxo-pregnane compound. The introduction is normally carried out in several steps, usually by direct or indirect halogenation and subsequent exchange of the halogen for an acyloxy group. A number of variants of this method is reviewed in C. Djorassi (Editor): Steroid Reactions, pp. 578–586, Holden-Day, San Francisco, 1963. Their drawback is, however, that they are suitable only for the thermodynamically more stable 20-oxo compounds of the 17β-series, whereas the 17α-isomers undergo at least partial rearrangement under the reaction conditions to form the 17α-compounds. It is also possible to start from a steroid 17-carboxylic acid, which reacts in the form of the corresponding acid chloride with diazomethane to yield the corresponding diazoketone (a 21-diazo-20-oxopregnane compound). Treatment of this diazoketone with a suitable carboxylic acid, preferably acetic acid, yields the desired final product, a 21-acyloxy-20-oxopregnane compound. This method too (cf. the above mentioned survey) is suitable, for all intents and purposes, only for isomers of the 17β-series, as the 17α-carboxylic acids can only be obtained by troublesome indirect means. It can be stated quite generally that no reliable systematic method of obtaining these thermodynamically less stable α-isomers is available, although these compounds are potentially of pharmacological interest.

The process of the present invention, however, does not have the drawback referred to above and can yield products both of the β- and α-configuration. Firstly, the steroid carbaldehydes used as starting materials are readily obtainable in both configurations, as will be described in more detail hereinafter, and secondly, these starting materials are prepared by conversion of corresponding 17-oxosteroids, i.e. compounds which can also be easily obtained by total synthesis. (The fact that the total synthesis of steroids is steadily increasing in importance makes the process of this invention particularly valuable as a very advantageous means of obtaining steroids with the hydroxyacetyl side chain of the pregnane series by total synthesis). Thirdly, the reaction proceeds without partial isomerisation of the decisive configuration in the 17-position and thus makes possible a less complicated isolation of the final product.

This last-mentioned fact is particularly surprising, as by analogy with the known prior art, for example that indicated above, it was to be expected that the use of a strongly basic medium in the first step and of the strongly acid medium is the second, woud lead in each case to enolisation and consequently to isomerisation of the side chain in the thermodynamically more stable configuration. That this does not happen, and that the decisive configuration of the starting material is maintained in the final product, belongs to the most important and completely unexpected advantages of the process of the invention.

The reagent for the first step of the process is known per se and its preparation has been described, cf. K. Ogura and c. Tsuchibashi, Tetrahedron Letters 1972, No. 26, pp. 2681–2684. The use of the reagent for the synthesis of individual simple α-hydroxyaldehydes is also discussed in this publication, but without any convincing conclusions on general applicability. The reagent is prepared by reacting the formaldehyde dimethylmercaptal-S-oxide ($CH_3.S.CH_2SO.CH_3$) with a hydrocarbyl alkali metal compound in an aprotic solvent. The preferred alkali metal is lithium; but sodium or potassium can also be employed. The hydrocarbyl radical in the organometal compound is, for example, an aryl radical, in particular a monocyclic aryl radical, preferably phenyl, or a lower alkyl radical, in particular a primary alkyl radical, most particularly butyl. Preferred organometal compounds (hydrocarbyl alkali metal compounds) are phenyllithium and, in particular, butyllithium. Suitable aprotic solvents for the preparation of the reagent are, in particular, hydrocarbons and ethers, preferably those whose boiling point is below 125° C. Preferred hydrocarbons are saturated aliphatic or cycloaliphatic hydrocarbons, in particular pentane, hexane, heptane and cyclohexane, and aromatic hydrocarbons, in particular benzene. Preferred ethers are, on the one hand, aliphatic ethers, especially diethyl ether and 1,2-dimethoxyethane, and on the other hand, cyclic ethers, such as tetrahydropyrane, dioxane and, in particular, tetrahydrofurane. Combinations of two or more of these solvents can also be used. The reagent is normally prepared by addition of a solution of the organometal compound to a solution of formaldehyde dimethylmercaptal-S-oxide at a temperature below 0° C., normally at about −25° C. to about −15° C. An excess of organometal compound is particularly to be avoided. To this solution of the reagent prepared in situ is then added the steroid aldehyde, usually in the form of a solution in one of the solvents mentioned. The reaction temperature varies between about −50° and +50° C. and is preferably in the range between about −20° and 0° C. When the reaction is complete, i.e. after about 1 to 24 hours depending on the reaction conditions, the primary reaction mixture is decomposed with water and further processed in the conventional manner. It is advisable to observe the customary measures for handling organometal compounds both during the preparation of the reagent and during the actual condensation, for example to avoid traces of protic solvents, especially of alcohols and water, also in the form of atmospheric moisture, and to carry out the reaction in an inert gas atmosphere, especially in an argon atmosphere. This reaction results in a product whose side chain is characterised by the partial formula

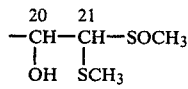

As in the side chain both the C-atom in the 20-position (on account of the hydroxyl group) and the C-atom in the 21-position (on account of the two sulfur-containing groups) are asymmetrical, i.e. they can have either the absolute configuration R or S, the true reaction product is a mixture of several of the four possible stereoisomers (i.e. 20R,21R-; 20R,21S-; 20S,21R-; and 20S,21S-) which can be present in varying, unspecific ratio. However, this circumstance does not constitute a drawback for the further processing in the second process step, as all four isomers yield the same final product. Any separation of the isomers from the mixture is therefore unnecessary.

During the reaction according to the first reaction step it is advantageous to protect the other oxo groups which may be present in the starting material, in particular the 3-oxo group, but also for example the 11-, 12-, 18- or 19-oxo group, against an undesired reaction. Conventional measures are employed to afford temporary protection of the oxo groups: for example, the oxo group is reduced to the hydroxyl group and subsequently recovered by oxidation, or, in particular, converted into a base-resistant functional derivative and subsequently liberated in conventional manner, for example by hydrolysis. (In particular, the starting material can contain these oxo groups in such a protected form from the previous stages of its prior manufacture).

Suitable base-resistant functional derivatives for protecting the oxo groups are, in particular, ketals and acetals, or thioketals and thioacetals. Preferred ketals and acetals are those derived from lower alkanols, such as methanol or ethanol, and, in particular, from 1,2- or 1,3-lower alkanediols, such as 1,2- or 1,3-prepanediol, 1,2- or 2,3-butanediol, and especially ethylene glycol. Suitable thioketals and thioacetals are those which are derived from sulfur analogues of the alkanols and especially diols already referred to. Ethylenedithio derivatives are particularly preferred. The 3- and 19-oxo groups are preferably protected as ketals and, in particular, thioketals, of the indicated kind.

The ketalising of thioketalising, or acetalising or thioacetalising, of the oxo groups to be protected is carried out in a manner known per se, especially under the conditions of acid catalysts and, if desired, using dehydrating agents or azeotropic distillation. The reagent employed is normally an alcohol or thiol as mentioned above or a reactive derivative thereof, for example an acetal or a ketal, or thioacetal or thioketal, in particular one in which the carbonyl component is readily volatile, for example 2,2-dimethyl-1,3-dioxolane or 2,2-dimethyl-1,3-dithiolane.

The removal of these protective groups is effected in a manner known per se by hydrolysis, preferably under the general conditions of acid catalysis. Thioketals and thioacetals are removed preferably under as mildly acidic conditions as possible, but with the addition of a compound which binds sulfur, for example a metal salt, in particular a heavy metal salt, such as cadmium carbonate and/or mercury(II) chloride. As this latter compound causes acid reaction in the presence of water, no additional acid is necessary as catalyst when using it.

If a sulfur-containing derivative has been used for the temporary protection of the oxo groups, it is advantageous to remove the protective group before the second process step in order to avoid complications in setting free the terminal aldehyde group.

If an oxo group is to be temporarily protected by conversion into a hydroxyl group, conventional methods are employed to this end, in particular reduction, for example with diborane or complex hydrides, such as lithium aluminium hydride or sodium borohydride. Conventional methods are also employed to accomplish the regeneration of the oxo group by the subsequent oxidation (or dehydrogenation) of the hydroxyl group. Preferred oxidising agents are compounds of hexavalent chromium, in particular chromium trioxide, as well as chromic acid and its alkali metal salts; reaction medium there are preferably used lower alkanecarboxylic acids, such as acetic and propionic acid, or pyridine or acetone, and optionally, as a diluent, a halogenated lower alkane, such as dichloromethane or chloroform; preferably the reaction temperature is kept below room temperature. This kind of protection is suitable in particular for the 11-oxo group, which is then in the form of the 11α- or especially 11β-hydroxy group during the reaction, in which case it can be introduced beforehand, for example during the manufacture of the starting material.

The second step of the process of the invention consists in treating the isomer mixture obtained in the first step with a strong inorganic hydrolysing agent, for example with a strong inorganic oxygen-containing acid, such as phosphoric acid, sulfuric acid or perchloric acid, or with a hydrohalic acid, in particular hydrochloric acid, or also with an organic sulfonic acid, such as methanesulfonic acid, benzenesulfonic acid, toluenesulfonic acid, p-bromo- or p-chlorobenzenesulfonic acid. The reaction is carried out in the presence of water in a conventional organic solvent, preferably a water-miscible solvent or solvent mixture normally used in acid hydrolysis. The conventional desulfurising agents normally employed in the hydrolysis of thioketals, for example cadmium and mercury salts, are not necessary in this reaction. The reaction temperature is in the range from about 0° C. to about 100° C., but is preferably in the region of room temperature. Depending on the respective conditions (temperature, concentration of the acid and starting material solvent etc.), the reaction time is from about ½ hour to 24 hours. In the course of this acid treatment, the sulfur-containing substituents in 21-position of the side chain having the partial formula —CH(OH)—CH(SCH$_3$)SOCH$_3$ are eliminated and the α-hydroxyaldehyde of the partial formula —CH(OH)—CH=O is liberated and immediately isomerised under the reaction conditions, probably via an enol, to the desired 21-hydroxy-20-oxo final product of the partial formula —CO—CH$_2$OH.

If desired, the final products can also be isolated in the form of corresponding 21-esters, i.e. after a subsequent conventional esterification (see below).

The final products obtained by the process of the invention have the general formula $$St(H)-CO-CH_2OH \qquad (I)$$

wherein St represents a divalent steroid radical of the general formula

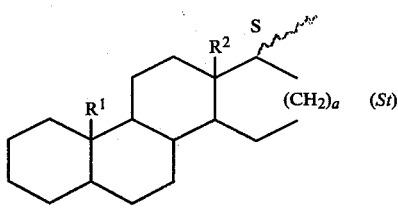

wherein n is 1 or 2, $R^1$ represents a hydrogen atom, methyl, a free, esterified or etherified hydroxymethyl group, a free or functionally modified formyl group, or a free or esterified carboxyl group, and $R^2$ represents an unsubstituted or a halogenated lower aliphatic hydrocarbon radical of 1 to 3 carbon atoms, a free, esterified or etherified hydroxymethyl group, a free or functionally modified formyl group, or a free or esterified carboxyl group, and wherein double bonds, halogen atoms, lower alkyl radicals, methylene bridges, free or functionally modified oxo groups and/or oxido groups, and also a 3α,5-trans-annular simple C-C bond of a cyclosteroid, singly or in advantageous combinations, can be present in one or more of the positions 1–16. The wavy lines in the above formula denote in particular that the side chain can be both α- and β-oriented. Double bonds are present preferably in the 1,2-, 4,5-, 5,6-, 5,10-, 6,7- and/or 9,11-positions, hydroxyl groups in the 3α-, 6β-, 7α-, 11α-, 12α- and especially 3β- and 11β-position, halogen atoms, in particular chlorine and fluorine atoms, in the 6α-, 9α- and 11β-position, lower alkyl radicals, in particular methyl radicals, in the 2α-, 6α-, 7α-, 16α- and 16β-positions, the oxo groups in the 3- and/or 11-position, and the oxido group in the 5α,6α-, 5β,6β-, 6α,7α-, 9α-11α-, 11,18- and 6β-19-positions. Among the particularly preferred advantageous combinations of the substituents in the rings A and B are, for example, a free or esterified 3β-hydroxy-5-ene or 3β-hydroxy-6β,19-oxido-5α grouping, a free or etherified 3-hydroxy-1,3,5(10)-triene and 3α,5α-cyclo-6β-hydroxy grouping, and a free, ketalised or thioketalised 3-oxo-4-ene and 3-oxo-4,6-diene grouping. Particularly preferred functional groups in the ring C which can be further combined with those of the rings A and B are the 9,11-double bond, the 9β,11β-oxido group and the 11β-hydroxyl group. Special mention is also to be made of the 18→11β-lactone bond and the oxidic bridge 11β,18 of the hemiketal form of the 18-aldehydo group occurring for example in aldosterone.

The term "lower" used to qualify an organic radical in this specification denotes that the radical in question contains not more than 7, preferably not more than 4, carbon atoms. Preferably n is 1.

A lower alkyl radical is, for example, a n-propyl, isopropyl, n-butyl, isobutyl, sec-butyl, tert-butyl radical, a branched or preferably straight chain pentyl, hexyl, radical, but especially an ethyl or methyl radical. A lower aliphatic hydrocarbon radical is a lower alkyl radical, for example one of those previously referred to, which can additionally contain one or two multiple bonds, i.e. double bonds, or acetylene bonds, for example a vinyl, allyl, propadienyl, propargyl and ethynyl radical.

The above lower aliphatic hydrocarbon radical (lower alkyl radical) can be substituted by one or more halogen atoms, in particular by fluorine and/or chlorine atoms, in which case it is for example a trifluoromethyl, difluoromethyl or 2-chlorovinyl radical.

A functionally modified oxo group or formyl group is in particular a ketalised or acetalised, or thioketalised or thioacetalised, oxo or formyl group, for example one which is used for the temporary protection described hereinbefore.

An etherified hydroxyl group can be a lower alkoxy group, especially a straight chain lower alkoxy group, for example the methoxy, ethoxy, propoxy and butoxy group; but in particular it is a hydroxyl group which is etherified by an easily removable protective group. Illustrative examples of such protective groups are in particular: a lower alkyl radical substituted in the 1-position by aryl, in particular phenyl, for example a benzyl- and triphenylmethyl radical; a lower alkyl radical substituted in the 1-position by lower alkoxy groups, such as those cited above, for example the 1-butoxyethyl or 1-methoxyethyl radical; heterocyclic radicals of the 2-tetrahydrofuryl and, in particular, 2-tetrahydropyranyl type; and, finally, a silyl group trisubstituted by the same or different hydrocarbon radicals, in particular a tri-lower alkyl-silyl group, for example the trimethylsilyl and dimethyl(tert-butyl)silyl group.

An esterified hydroxyl group is in particular a hydroxyl group esterified by a carboxylic acid, or a lactonised hydroxyl group, which is esterified by a carboxyl group which is a part of the same molecule.

The carboxyl component of an esterified hydroxyl group can be derived in particular from the carboxylic acids customary in steroid chemistry, for example monocarboxylic acids containing not more than 18 carbon atoms, such as aliphatic carboxylic acids, in particular formic acid and lower alkanecarboxylic acids, the lower alkyl moiety of which is one of those cited above, primarily propionic, butyric, isobutyric, valeric, isovaleric, enanthic and diethylacetic acid, and, most particularly, caproic, trimethylacetic acetic acid, and also corresponding halogenated lower alkanecarboxylic acids, such as chloroacetic acid, trichloroacetic or trifluoroacetic acid, and also cycloaliphatic, cycloaliphatic-aliphatic and aromatic carboxylic acids, for example benzoic acids which are unsubstituted or substituted by halogen, such as fluorine, chlorine or bromine, hydroxyl, lower alkoxy, lower alkyl and/or nitro, or corresponding aryl- or aryloxy-lower alkanecarboxylic acids, and corresponding dicarboxylic acids containing not more than 12 carbon atoms, for example succinic, glutaric, adipic and phthalic acid.

By an esterified carboxyl group is meant not only a carboxyl group which is in the form of its ester with an alcohol, in particular one with a lower alkanol, but also a carboxyl group which closes a 6-membered or 5-membered lactone ring with a hydroxyl group which is present in the same molecule at the corresponding distance.

The steroid aldehydes used as starting materials in the process of the present invention have the general formula

 St(H)—CH=O (II)

wherein St is as previously defined. Where these starting materials are not already known, they can be obtained by generally known methods, for example by the Wittig reaction of a corresponding 17- or 17a-oxo compound with methoxymethylenetriphenylphosphane or an analogous reagent, and by the subsequent acid-catalysed hydrolysis of the intermediate 17- or 17a- methoxymethylene compound. (This method, however, affords only the thermodynamically stable isomer).

In a preferred variant of the process, starting materials are employed which have been prepared by a special and particularly advantageous combination of processes which are known per se. This special embodiment of the process of the present invention consists in converting a ketone of the general formula $$St=O \qquad (III)$$

wherein St has the above meaning, initially by reaction with tosylmethylisocyanide (Ts—CH$_2$—N≡C) into a corresponding cyano steroid of the general formula $$St(H)—C≡N$$

wherein St has the given meaning, reducing this cyano steroid in a manner known per se, for example with diisobutylaluminium hydride or an analogous reducing agent, to the corresponding steroid carbaldehyde of the above formula II, and subsequently converting this latter by the main process described at the outset into the final product of the general formula I above. Preferably all oxo groups present in the molecule and not participating in these reactions are temporarily protected during the reactions, preferably in the manner described for the main process above. It is advantageous to extend this protection not only to the formation of the cyano compound and its reduction, but also to the subsequent treatment with the metallated reagent.

The reaction of the oxo compound of the formula III with tosylmethylisonitrile is carried out in a manner known per se, in particular by the method described in Tetrahedron 31, 2151 and 2157 (1975). The product is usually a mixture of α- and β-isomers which can be isolated as individual compounds by conventional physical methods of separation. This mode of manufacture is of the greatest interest as a general method of obtaining the α-isomers (i.e. the thermodynamically less stable isomers), which are otherwise very difficult to obtain.

The reduction of the cyano compounds of the formula IV to the carbaldehyde of the formula II is also carried out in a manner known per se, in particular with diisobutylaluminium hydride of the formula [(CH$_3$)$_2$CHCH$_2$)$_2$]AlH, by a method analogous to that described in J. Org. Chem. 29, 3046 (1964) and J. Org. Chem. 35, 858 (1970). This method is also advantageous because, when carrying it out conventionally, no epimerisation of a less stable 17α-carbaldehyde to its 17β-isomer takes place, although such a complication was to be expected.

Among other things, the process of the invention is an advantageous variant for the manufacture of aldosteroneantagonising 19-oxygenated 21-hydroxy compounds of the pregnane series, which are described in Belgian patent specification 867,634 (Case 4-11164).

The present invention also relates to those process products of the general formula I which are novel. These products are either in the form of the α- and β-isomers or else in the form of their 21-esters, especially esters of the carboxylic acids conventionally employed in steroid chemistry and singled out for special mention at the outset. The esters are obtained, if desired, by subsequent conventional acylation of the free 21-hydroxyl group in the primary final products of the formula I with a corresponding acid or a reactive derivative thereof, such as an anhydride or acid halide.

Particularly preferred novel compounds are those of the formula

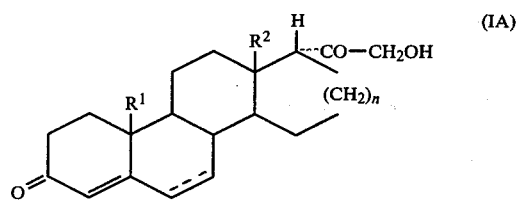

wherein n, R$^1$ and R$^2$ have the given meanings, and their 6,7-dehydro derivatives, and, among these compounds, in particular those wherein R$^2$ represents methyl or difluoromethyl, and R$^1$ represents hydroxymethyl, methoxymethyl, acetoxymethyl or hydrogen, and, if n is 2 and/or R$^2$ is difluoromethyl, R$^1$ also represents methyl, and, most particularly, those compounds wherein n is 1. All these compounds can also be in the form of their 21-esters, in particular of those already singled out for special mention, chiefly as acetates.

These particularly preferred compounds are not only useful as valuable intermediates for the manufacture of pharmacologically useful compounds, for example their β-isomers, but themselves possess valuable physiological properties, especially as agonists and antagonists of natural hormones of warm-blooded animals, in particular humans. Accordingly, for example, 19,21-dihydroxy-17α-pregn-4-ene-3,20-dione has a pronounced antigestagenic action, as can be demonstrated for example in the modified Clauberg-McPhail test on infant female rabbits treated with oestrogen and afterwards with progesterone, especially in local intra-uterine administration. The compounds can therefore be used in hormonal therapy for regulating the level of sexual hormones and adrenocortical hormones. Thus, for example, 19,21-dihydroxy-17α-pregn-4-ene-3,20-dione can be used as such or in the form of an ester, such as a monoacetate and especially the diacetate, for suppressing the effects of progesterone and is consequently particularly suitable for preventing conception, in particular as a post-coital contraceptive. Corresponding 6,7-dehydro analogues, especially 19,21-dihydroxy-17α-pregna-4,6-diene-3,20-dione, have similar properties and utility.

The present invention, especially in conjunction with the process and its particular embodiments, relates not only to steroids of the preferred D-series occurring in nature, but also to the corresponding antipodes of the L-series and to racemic mixtures of both antipodes which occur in the total synthesis of steroids. Throughout this specification, the term "steroid" is to be understood in this sense.

The invention also relates to those embodiments of the above process in which a compound obtained as intermediate in any stage is used as starting material and the missing steps are carried out, or in which a starting material is formed under the reaction conditions.

The present invention also relates to preparations containing at least one novel compound of the formula I or IA which are used for the treatment of disorders of the hormonal functions of different form. They contain an effective amount of the active substance alone or in admixture with inorganic or organic, solid or liquid, pharmaceutically acceptable carriers, and, if desired, also with other pharmacologically or therapeutically valuable substances, and are suitable especially for enteral, for example oral or rectal, or for parenteral administration.

Throughout the entire remainder of this description, the term "active substance" shall be understood to mean a compound of the formula I, and especially formula IA, as defined above in connection with the general and especially specific meanings.

The present invention relates in particular to pharmaceutical compositions containing as active substance at least one of the compounds of the formula IA (including 6,7-dehydro derivatives and 21-esters) according to the invention in the form of a sterile and/or isotonic aqueous solution, or in admixture with at least one solid or semi-solid carrier.

The present invention also relates to medicinal preparations in the form of dosage units that contain at least one of the compounds according to the invention alone or in admixture with one or more adjuncts, especially medicinal preparations in solid form.

The invention relates in particular to medicinal preparations in the form of tablets (including lozenges, granules and pastilles), sugar-coated tablets, capsules, pills, ampoules, dry vials or suppositories containing at least one of the active substances of the formula I alone or in admixture with one or more adjuncts.

The term "medicinal preparation" is used in this description to denote individual separate portions of homogeneous composition that are suitable for medicinal administration. The expression "medicinal preparation in the form of dosage units" is used in this description to denote individual separate portions of homogeneous compositions that are suitable for medicinal administration and that each contain a specific amount of the active substance of the invention corresponding to about 0.025 to about 4, preferably about 0.1 to about 1, daily dose.

The adjuncts for use in the pharmaceutical compositions (for example granulates) for the production of tablets, sugar-coated tablets, capsules and pills are, for example, the following:
  (a) diluents, for example starch, sugars, such as lactose, glucose and saccharose, mannitol, sorbitol and silica;
  (b) binders, for example carboxymethylcellulose and other cellulose derivatives, alginic acid and its salts, such as sodium alginate, gelatin, and polyvinylpyrrolidone;
  (c) moisture regulators, for example glycerol;
  (d) disintegrators, for example agar-agar, calcium carbonate and sodium bicarbonate;
  (e) retardants for slowing down the absorption of the active substance, for example paraffin;
  (f) accelerators for the resorption, for example quaternary ammonium compounds;
  (g) surfactants, for example cetyl alcohol and glycerin monostearate;
  (h) adsorbents, for example kaolin and bentonite;
  (i) glidants and lubricants, for example talcum, calcium stearate, magnesium stearate and solid polyethylene glycols.

These and similar adjuncts can also be used for several of the above-mentioned purposes.

The tablets, sugar-coated tablets, capsules and pills containing the above-mentioned pharmaceutical compositions according to the invention can be provided with the customary coatings and coating materials with which, if desired, dyes or pigments, for example for identification or characterisation purposes, are admixed. These coatings can also be of a composition that makes possible a retarded release of the active substance; waxes and cellulose preparations, such as acetylcellulose phthalate or hydroxypropylmethylcellulose phthalate, for example, are suitable for this purpose.

These compositions can also be processed to microcapsules.

Medicinal preparations for parenteral administration are preferably ampoules containing a single dose of the active substance of the invention, especially a water-soluble, physiologically tolerable salt, in the form of an aqueous solution that is preferably sterilised, and they optionally contain the usual buffers and/or neutral inorganic salts such as sodium chloride, as adjwants for adjusting the isotonicity with blood. An aqueous solution of this type is also particularly suitable for the production of injectable solid forms of medicinal preparation, such as dry vials into which the quantity of solution corresponding to the single dose is evaporated in the usual manner, for example by lyophilisation, and the solid residue is brought into the injection solution, with sterile water, only immediately before use.

Suitable adjuncts for pharmaceutical compositions to be processed into suppositories are the customary suppository base materials, for example natural or synthetic triglycerides, such as cocoa butter, paraffin hydrocarbons, polyethylene glycols and higher alkanols. Gelatin rectal capsules contain as base material, for example, liquid triglycerides, polyethylene glycols or paraffin hydrocarbons.

The pharmaceutical compositions of the invention preferably contain from about 0.1 to about 99.5%, especially from about 1 to about 90%, by weight of the active substance.

The recommended daily dosage for a warm-blooded animal weighing 75 kg is approximately 5–500 mg, preferably approximately 20–300 mg, but it can vary within wide limits depending on species, age and the individual response.

The production of the above-mentioned pharmaceutical compositions, preparations, medicinal preparations and medicinal preparations in the form of dosage units according to the invention is carried out by means of conventional manufacturing processes in the pharmaceutical industry that are known per se, for example by means of customary mixing, granulating, tabletting, sugar-coating and dissolving and lyophilising processes, which are carried out, if desired, under sterile conditions or an intermediate or an end product is sterilised.

The present invention also relates to the use of compounds of the formula I for combating a wide variety of hormonal disorders, especially disorders of the sex hormones, in man and other warm-blooded animals, and to a corresponding therapeutic method which comprises administering an effective dose of at least one of the active substances of the invention, alone or together with one or more pharmaceutical carriers or in the form of a medicinal preparation. The active substances of the invention are administered enterally, for example rectally or especially orally, or parenterally, such as intraperitoneally or intravenously.

The following Examples illustrate the invention further without limiting it.

EXAMPLE 1

(a) A solution of potassium tert-butoxide is prepared from 34 g of potassium and 980 ml of tert-butanol under an argon atmosphere; to this solution a solution of 45 g of 3,3-ethylenedithio-19-hydroxyandrosta-4,6-dien-17-one in 1000 ml of 1,2-dimethoxyethane is quickly added dropwise at room temperature under an argon atmosphere while stirring. After stirring for 15 minutes, a solution of 35.5 g of tosylmethyl isocyanide in 1000 ml of 1,2-dimethoxyethane is added to the reaction mixture over a period of 90 minutes at 25° C. and the mixture is stirred for a further hour and poured onto ice water. The organic layer is separated, the aqueous layer is extracted with methylene chloride and the combined organic extracts are washed with water, dried over sodium sulphate and concentrated in a water-jet vacuum. The residue is chromatographed over a silica gel column; elution with a mixture of hexane and ethyl acetate (4:1) yields 24 g of 3,3-ethylenedithio-17$\beta$-cyanoandrosta-4,6-dien-19-ol; melting point: 180°–181° C. after one crystallisation from methylene chloride/diisopropyl ether; $[\alpha]_D = 162°$ (c=0.14, chloroform). Further elution with the same solvent mixture yields 12 g of 3,3-ethylenedithio-17$\alpha$-cyanoandrosta-4,6-dien-19-ol; melting point: 211°–213° C. (crystallisation from methylene chloride/ethyl acetate); $[\alpha]_D = 61°$ (c=0.48, chloroform).

(b) 400 ml of a 20% solution of diisobutyl aluminium hydride in toluene is added dropwise at $-20°$ C. over a period of 15 minutes, while stirring, to a solution of 24 g of 3,3-ethylene-dithio-17$\beta$-cyanoandrosta-4,6-dien-19-ol in 450 ml of 1,2-dimethoxyethane, the mixture is allowed to warm to 25° C. and is stirred for a further hour at this temperature. The reaction mixture is poured onto ice water, acidified with hydrochloric acid and stirred for one hour. The product is taken up in methylene chloride, the organic phase is washed in succession with water, aqueous sodium bicarbonate solution and water, dried over sodium sulfate and concentrated in a waterjet vacuum. The residue is chromatographed over a silica gel column; elution with a mixture of toluene and ethyl acetate (95:5) yields 3,3-ethylenedithio-19-hydroxyandrosta-4,6-diene-17$\beta$-carboxaldehyde; melting point: 165°–166° C. (crystallisation from methylene chloride/diisopropyl ether), $[\alpha]_D = +198°$ (c=0.474, chloroform).

(c) 13.5 ml of a 1.6 molar solution of butyl lithium in hexane is added dropwise to a solution of 6.7 ml of formaldehyde dimethylthioacetal S-oxide (methylthiomethyl methyl sulfoxide) in 80 ml of tetrahydrofuran at $-20°$ C. under an argon atmosphere, so that the temperature does not exceed $-17°$ C. Subsequently a solution of 13 g of 3,3-ethylenedithio-19-hydroxyandrosta-4,6-diene-17$\beta$-carboxaldehyde in 100 ml of tetrahydrofuran is added dropwise to the reaction mixture over a period of 30 minutes and the mixture is stirred for a further 30 minutes. The reaction mixture is poured onto ice water and the product is taken up in ethyl acetate. The combined organic extracts are washed with water and a saturated aqueous sodium chloride solution in succession, dried over sodium sulfate, concentrated in a water-jet vacuum and the residue is applied to a column of silica gel. The unreacted starting material is recovered by elution with a mixture of hexane and ethyl acetate (1:1); using a mixture of ethyl acetate/acetone (2:1) fractions are eluted that after evaporation yield a crystalline mixture of isomeric 3,3-ethylenedithio-21$\xi$-methylsulphinyl-21$\xi$-methylthio-pregna-4,6-diene-19,20-$\xi$-diols, which is processed further without separation.

(c) 42 ml of water, 12 g of mercury(II) chloride and 12 g of cadmium carbonate are added to a solution of 15.9 g of the mixture of isomers obtainable according to (c) in 960 ml of acetone, and the mixture is stirred at room temperature for 5 hours and filtered through a layer of kieselguhr. The filter cake is extracted with methylene chloride, the extract is combined with the original filtrate and concentrated by evaporation. The resulting crude mixture of isomeric 19,20$\xi$-dihydroxy-21$\xi$-methylsulphinyl-21$\xi$-methylthiopregna-4,6-dien-3-ones is used directly in the next stage.

(e) 50 ml of 5 N hydrochloric acid is added to the isomer mixture of stage (d) dissolved in 300 ml of tetrahydrofuran, and the mixture is stirred for 13 hours at room temperature. The reaction mixture is poured onto 2 liters of ice-water and the product is taken up in methylene chloride. The combined extracts are washed with a dilute sodium carbonate solution, water and a saturated sodium chloride solution in succession, dried over sodium sulphate and concentrated in a water-jet vacuum. The residue is chromatographed over a silica gel column; elution with a mixture of hexane and acetone (2:1) yields 19,21-dihydroxypregna-4,6-diene-3,20-dione, which, after crystallisation from acetone/hexane, melts at 163°–165° C. The 17$\alpha$-cyano epimer (see step a) is processed in analogous manner in accordance with steps (b) to (e), yielding the 19,21-dihydroxy-17$\alpha$-pregna-4,6-diene-3,20-dione with a melting point of 192°–195° C. (crystallisation from chloroform/ethyl acetate).

EXAMPLE 2

In the same way as described in Example 1, 3,3-ethylenedithio-19-hydroxy-androst-4-en-17-one yields an isomer mixture from which 3,3-ethylenedithio-17$\beta$-cyano-androst-4-en-19-ol (m.p. 205°–206° C.) and the isomeric 3,3-ethylenedithio-17$\alpha$-cyano-androst-4-en-19-ol (m.p. 171°–172° C.) are isolated. This latter isomer is reduced to the amorphous 3,3-ethylenedithio-19-hydroxy-androst-4-en-17$\alpha$-carbaldehyde, which is converted into the isomer mixture of 3,3-ethylenedithio-21$\xi$-methylsulfinyl-21$\xi$-methylthio-17$\alpha$-pregn-4-ene-19,20$\xi$-diol, which in turn is hydrolysed to 19,21-dihydroxy-17$\alpha$-pregn-4-ene-3,20-dione with a melting point of 207°–212° C. The corresponding 19,21-diacetate melts at 124°–125° C. after recrystallisation from methylene chloride/methanol.

The 17$\beta$-nitrile affords, via analogous intermediates of the $\beta$-series, 19,21-dihydroxy-pregn-4-ene-3,20-dione with a melting point of (146° C.) 163°–168° C. The corresponding 19,21-diacetate melts at 124°–125° C. (with depression at the mixed melting point with the 17$\alpha$-epimer).

EXAMPLE 3

In the same way as described in Example 1, 3,3-ethylenedithio-18,18-difluoro-androst-4-en-17-one yields a mixture consisting of 3,3-ethylenedithio-18,18-difluoro-17$\beta$-cyano-androst-4-ene (m.p. 145°–146° C.) and 3,3-ethylenedithio-18,18-difluoro-17$\alpha$-cyano-androst-4-ene (m.p. 230°–232° C.). The crude product is reduced to a mixture of 3,3-ethylenedithio-18,18-difluoro-androst-4-ene-17$\beta$- and 17$\alpha$-carbaldehyde. This mixture is processed as described in steps (c), (d) and (e) of Example 1 and 21-hydroxy-18,18-difluoro-17$\alpha$-pregn-4-ene-3,20-dione (m.p. 165°–167° C.) and 21-hydroxy-18,18-difluoro-pregn-4-ene-3,20-dione (m.p. 140°–141° C.) are isolated from the resulting isomer mixture. Alternatively, both isolated 17-cyano compounds are processed separately.

EXAMPLE 4

In the same way as described in Example 1, 3,3-ethylenedithio-19-methoxy-androst-4-en-17-one yields an isomer mixture from which 3,3-ethylenedithio-17β-cyano-19-methoxy-androst-4-ene (m.p. 173°–174° C.) is isolated. This latter is reduced to the amorphous 3,3-ethylenedithio-19-methoxy-androst-4-ene-17β-carbaldehyde, which is further processed in accordance with steps (c) to (e) of Example 1, yielding 21-hydroxy-19-methoxypregn-4ene-3,20-dione with a melting point of 148°–149° C.

EXAMPLE 5

In the same way as described in Example 1, 3,3-ethylenedithio-7α-methyl-oestr-4-en-17-one yields 3,3-ethylenedithio-17β-cyano-7α-methyl-oestr-4-ene (m.p. 231°–323° C.), which is reduced to 3,3-ethylenedithio-7α-methyl-oestr-4-ene-17β-carbaldehyde and subsequently further processed in accordance with steps (c) to (e) of Example 1. The resulting 21-hydroxy-7α-methyl-19-norpregn-4-ene-3,20-diene melts at 160° C.

EXAMPLE 6

In the same way as described in Example 1, the following final products are obtained, starting from corresponding 17-oxo compounds:
(a) 21-hydroxy-pregna-4,6-diene-3,20-dione, characterised as 21-acetate, m.p. 113°–114° C.;
(b) 21-hydroxy-pregna-1,4,6-triene-3,20-dione, characterised as 21-acetate, m.p. 170°–172° C.;
(c) 21-hydroxy-pregna-4,6,9(11)-triene-3,20-diene, characterised as 21-acetate, m.p. 133°–134° C.;
(d) 21-hydroxy-2,2-dimethyl-pregn-4-ene-3,20-dione, m.p. 118°–120° C.;
(e) 21-hydroxy-16α-methyl-pregn-4-ene-3,20-dione, characterised as 21-acetate, m.p. 132° C.;
(f) 9α-fluoro-11β,21-dihydroxy-16α-methyl-pregna-1,4-diene-3,20-dione, m.p. 216°–222° C.;
(g) 21-hydroxy-19-nor-pregn-4-ene-3,20-diene, m.p. 136°–137° C.;
(h) 16α-ethyl-21-hydroxy-19-nor-pregn-4-ene-3,20-dione;
(i) 19,21-dihydroxy-pregna-4,6-diene-3,20-dione-19-acetate, m.p. 105°–107° C.;
(j) 21-hydroxy-3,20-dioxo-pregna-1,4-dien-18-al, characterised as 21-acetate, m.p. 158°–160° C.;
(k) 21-hydroxy-3,20-dioxo-pegna-4,6-dien-18-al, characterised as 21-acetate, m.p. 121°–122° C.;
(l) 18,21-dihydroxy-pregna-4,6-diene-3,20-dione, m.p. 170°–172° C., 21-acetate, m.p. 143°–144° C.;
(m) 21-hydroxy-3,20-dioxo-pregn-4-en-19-al, m.p. 162°–164° C.;
(n) 21-hydroxy-3,20-dioxo-pregna-4,6-dien-19-al, m.p. 164°–166° C.;
(o) 21-hydroxy-19-methoxy-pregna-4,6-diene-3,20-diene, characterised as 21-acetate, m.p. 158°–166° C.;
(p) 3,21-dihydroxy-19-nor-pregna-1,3,5(10)-trien-20-ene, m.p. 190°–191° C.;
(q) 3β,21-dihydroxy-17α-methyl-D-homo-pregn-5-en-20-ene, m.p. 198°–202° C.; and
(r) 11β,21-dihydroxy-17α-methyl-D-homo-pregn-4-ene-3,20-dione, m.p. 198°–200° C.

What is claimed is:
1. A process for introducing a 17α- or β-oriented hydroxyacetyl side chain of a 21-hydroxy-20-oxo-pregnane of formula I

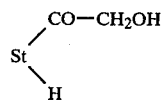
(I)

in which St represents a divalent steroid radical of the formula

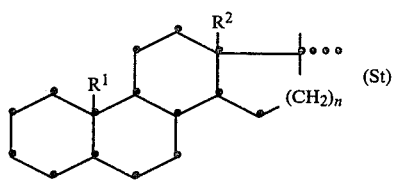
(St)

in which n is 1 or 2, $R^1$ represents a hydrogen atom, methyl, a free, esterified or etherified hydroxymethyl, formyl, a formyl protected as acetal or thioacetal, or a free or esterified carboxyl and $R^2$ represents an aliphatic hydrocarbon radical of 1–3 carbon atoms, a halogenated aliphatic hydrocarbon radical of 1 to 3 carbon atoms, a free, esterified or etherified hydroxymethyl, formyl, a formyl protected as acetal or thioacetal, or a free or esterified carboxyl, and in which the St radical may contain in addition one or more double bonds, halogen atoms, lower alkyl radicals, methylene bridges, free oxo groups, oxo groups protected as ketal or thioketal and/or oxido groups, and also a 3α,5-trans-annular simple C-C bond of a cyclosteroid, singly or in combination, at one or more of the positions 1–16, which process comprises:
(a) treating a corresponding carbaldehyde of the formula II

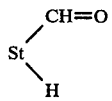
(II)

in which St is the above divalent steroid radical wherein n, $R^1$ and $R^2$ have meaning as defined above with the proviso that $R^1$ does not represent free formyl, $R^2$ does not represent free formyl or free oxo groups, and the St radical does not contain free oxo groups with formaldehyde dimethylmercaptal S-oxide of the formula

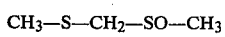

in the form of an alkaline metal salt thereof in an aprotic solvent at a temperature of −50° to +50° C., and
(b) hydrolyzing the resulting intermediate of the formula

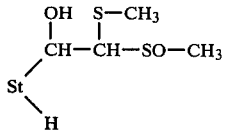

in which St has the last said meaning, with a strong acid in the presence of water at a temperature of 0° to 100° C.

2. A process according to claim 1, wherein the starting steroid carbaldehyde of the formula II as defined in claim 1 is obtained by reacting a ketone of the formula III $$St=O \qquad (III)$$

wherein St has the meaning as defined for formula II in claim 1 with tosylmethyl isocyanide and reducing the resulting steroid of the formula

with diisobutyl aluminum hydrides.

3. A process according to either claim 1 or 2 wherein any oxo or formyl group in the radical St is protected as a thioketal or a thioacetal of 1,2-ethanedithiol.

4. A process according to claim 1, wherein a protective thioketal or thioacetal group is removed before the final step (b) by mild acid hydrolysis in the presence of a heavy metal salt.

5. A process according to claim 1, which further comprises acylating the final product of the formula I to obtain a 21-ester thereof with a carboxylic acid having not more than 18 carbon atoms.

6. The process of claim 1, wherein a double bond is present in the 1,2-; 5,6-; 5,10-; 6,7-- and/or 9,11-position of the St moiety of formula I.

7. The process of claim 1, wherein a hydroxyl group is present in $3\beta$- or $11\beta$-position of the St moiety of formula I.

8. The process of claim 1, wherein a $3\beta$-hydroxy-5-ene or 3-hydroxy-1,3,5(10)-triene grouping is present in the St moiety of formula I.

9. The process of claim 1, wherein the 3-oxo-4-ene or 3-oxo-4,6-diene grouping is present in the St moiety of formula I.

10. The process of claim 1, wherein the 9,11-double bond or the $11\beta$-hydroxyl group in addition to the 3-oxo-4-ene or 3-oxo-4,6-diene grouping is present in the St moiety of formula I.

11. The process of claim 1, wherein methyl is present in the $2\alpha$-, $6\alpha$, $16\alpha$- and/or $16\beta$-position of the St moiety of formula I.

12. The process of claim 1, wherein $n=1$ in the St moiety of formula I.

13. The process of claim 1, wherein the hydroxyacetyl side chain $-CO-CH_2-OH$ is $\alpha$ oriented in the formula I.

14. The process of claim 13, wherein the 3-oxo-4-ene or 3-oxo-4,6-diene grouping is present in the St moiety; $R^1$ represents hydrogen, methyl, hydroxymethyl, methoxymethyl or acetoxymethyl; $R^2$ represents methyl or difluoromethyl; and $n=1$.

* * * * *